United States Patent [19]

Muench et al.

[11] 4,190,605

[45] Feb. 26, 1980

[54] CATALYST ACTIVATION IN OXIDATION PROCESS

[75] Inventors: Wayne C. Muench; Glen O. Strand; Thad S. Hormel, all of Midland, Mich.

[73] Assignee: The Dow Chemical Company, Midland, Mich.

[21] Appl. No.: 920,883

[22] Filed: Jun. 30, 1978

[51] Int. Cl.² .............................................. C07C 45/16
[52] U.S. Cl. ................................ 260/600 R; 252/447
[58] Field of Search ............................ 260/600 R, 603

[56] References Cited

U.S. PATENT DOCUMENTS

| 3,321,526 | 5/1967 | Marchand et al. | 260/600 |
|---|---|---|---|
| 3,673,257 | 6/1972 | DiBella | 260/600 |
| 4,026,950 | 5/1977 | Ludec | 260/600 |

OTHER PUBLICATIONS

Heyns et al., Tetrahedron, vol. 9, (1960), 67–75.

*Primary Examiner*—Bernard Helfin
*Attorney, Agent, or Firm*—Joyce P. Hill; Douglas N. Deline; Lester J. Dankert

[57] ABSTRACT

A noble metal catalyst, such as palladium, is activated by successive and sequential reactions with an alcohol, such as hydroxybenzyl alcohol, and oxygen or a gas containing oxygen in an aqueous, preferably alkaline, medium, The catalyst activated in the aforementioned manner is particularly useful for the oxidation of alcohols to the corresponding aldehydes.

6 Claims, No Drawings

CATALYST ACTIVATION IN OXIDATION PROCESS

BACKGROUND OF THE INVENTION

The oxidation of hydroxybenzyl alcohol by means of air or pure oxygen in the presence of a catalyst based on a noble metal such as platinum or palladium has been reported.[1] The oxidation is generally carried out in the liquid phase in an aqueous, preferably alkaline, medium. In the case of ortho-hydroxybenzyl alcohol, the oxidation in an aqueous alkaline medium containing about 1 percent by weight of noble metal relative to the alcohol to be oxidized gives salicylaldehyde with yields which are between 70 and 80 percent, relative to the alcohol employed. However, it is found that this oxidation method needs extended reaction times, of up to 45 hours, to give a high degree of conversion to the aldehyde. The addition of boric acid or a borate in substantially equimolecular quantities in relation to the hydroxybenzyl alcohol to be oxidized, reportedly speeds up the oxidation without promoting the formation of secondary products.[2] However, this process using the boric acid or borate additives requires a reaction time from one to several hours depending upon the starting material employed.

[1] Marchand et al., U.S. Pat. No. 3,321,526 (May 23, 1967).
[2] Note 1, supra.

Another method of oxidizing the hydroxybenzyl alcohols to the hydroxybenzaldehydes comprises liquid phase oxidation of the corresponding hydroxybenzyl alcohol with molecular oxygen or of a gas containing molecular oxygen in an aqueous medium containing an alkaline agent, in the presence of a platinum or palladium catalyst and in the presence of a cocatalyst containing bismuth.[3] The use of the platinum/bismuth catalyst system reportedly gives a significant improvement both in respect of the rate of reaction and in respect of the yields of aldehyde; it also makes it possible to significantly reduce the amount of noble metal usually employed.

[3] Ludec, U.S. Pat. No. 4,026,950 (May 31, 1977)

Hence, the prior art methods usually require a long reaction time with resulting low productivity or require the use of additives, e.g., bismuth compounds, boric acid or borate compounds in order to obtain shorter reaction times or better selectivity of the oxidation reaction. It would be desirable to prepare aldehydes from the corresponding alcohols in a more frugal and expeditious manner.

SUMMARY OF THE INVENTION

The present invention provides a novel process for activating noble metal catalysts, especially palladium on charcoal catalysts, useful in the oxidation of alcohols, especially hydroxybenzyl alcohols, to the corresponding aldehydes. The catalyst is activated by successive and sequential reactions with an alcohol, such as hydroxybenzyl alcohol, and molecular oxygen in an aqueous, preferably alkaline, medium. The resulting activated catalyst is useful in effecting oxidation of alcohols such as hydroxybenzyl alcohols with fast reaction rates and good selectivity to the corresponding aldehydes in excellent yields.

DETAILED DESCRIPTION OF THE INVENTION

The activity, selectivity and stability of the noble metal catalyst used in the air-oxidation of hydroxybenzyl alcohols is improved in a pre-treatment process wherein successive and sequential reactions of the catalyst with the starting reactants are conducted. For example, a palladium-on-charcoal catalyst is used to completely oxidize several batches of basic aqueous feed containing o- and p-hydroxybenzyl alcohols before the large-scale or long-term production of the corresponding aldehydes is operational. A sufficient number of batches of feed is oxidized in this pre-treatment process until the rates of ortho- and para-oxidation are nearly equal; the noble metal catalyst is thereby conditioned (i.e., activated and more efficient in catalyzing the formation of the desired aldehyde products).

With regard to the noble metals used for catalyzing the reaction, platinum and palladium are preferred. They may be in various forms such as, for example, platinum black, palladium black, platinum oxide, palladium oxide, or the noble metal deposited on various supports such as charcoal, calcium carbonate, activated aluminas and silicas, or equivalent materials. Catalyst compositions based on charcoal are particularly suitable.

The surprising and unexpected phenomena that is the essence of this invention is the change in activity of the noble metal catalyst resulting from the catalyst pre-treatment. The catalyst does not behave the same when it is new as it does after a few successive and sequential oxidation reactions with the starting materials. The air-oxidation reaction of phenolic alcohols in this invention may be represented as follows:

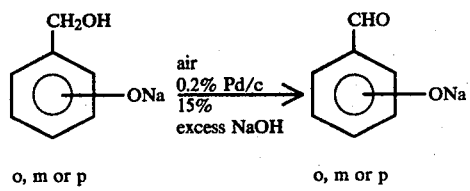

o, m or p        o, m or p

Prior to the oxidation reaction, the phenolic alcohols are maintained in an aqueous medium containing an alkali in solution and are therein converted to their alkali metal salts. In this context, sodium hydroxide or potassium hydroxide is generally employed as the alkaline agent. The proportion of alkali to be used can be between 1.0 and 1.3 moles per mole of phenolic compounds in solution. An excess, e.g., 15 percent molar excess, of caustic over organics is preferred. The concentration by weight of alcohol (o-hydroxybenzyl alcohol, p-hydroxybenzyl alcohol, 2,4-di(hydroxymethyl)-phenol) in the aqueous medium is usually between 5 percent and 25 percent and preferably between 10 percent and 20 percent.

In some embodiments, a batch process may be used which consists of bringing the aqueous solution containing the phenolic alcohol to be oxidized, the alkaline reagent, the noble metal catalyst, in the proportions indicated below, into contact with molecular oxygen or a gas containing the latter. The amount of catalyst to be employed in the reaction zone, expressed in weight of metallic platinum or metallic palladium relative to that of the alcohol to be oxidized, can vary from 0.20 to 2.0 percent and preferably from 0.5 to 1.0 percent. The process can be carried out at atmospheric pressure or super atmospheric pressure, as desired. The mixture is then stirred at the desired temperature until an amount of oxygen corresponding to that required to convert the alcohol to the aldehyde has been consumed.

In other embodiments, a stream of oxygen or a gas containing oxygen, preferably air, is passed into and through a treatment zone containing a fixed bed of the noble metal catalyst, concurrently with a stream of aqueous alkaline solution containing the phenolic alcohol to be oxidized. Variations in temperature, pressure, air flow rates, and catalyst load (or residence time) have a noticeable effect on reaction rates and yields. The kinetics of the oxidation reaction are complex and depend on many variables. However, the maximum possible rate of oxidation is limited by the rate of air flow into the system which is adjusted to an amount of oxygen corresponding to that required to convert the alcohol to the aldehyde.

In general terms, the reaction is carried out in a temperature range extending from 60° C. to 110° C. and preferably extending from 70° C. to 85° C.

The rate of reaction increases with pressure but not in a linear fashion. Since the reaction involves adsorption phenomena and depends on the fraction of adsorption sites occupied by reactant molecules, at low pressures the rate varies directly with pressure while at high pressures the rate is independent of pressure. The reaction can favorably be carried out at pressures from 60 to 120 lbs/square inch gauge (psig); from 120 to 180 psig the reaction rate increases only slightly suggesting that at 180 psig the reaction rate is essentially pressure independent.

Hydroxybenzyl alcohols suitable for this invention may be prepared by any known method, for example, condensation of phenol with formaldehyde in an alkaline solution (lederer, *J. Pr. Chem.*, 1894[ii], 50, 223. Manasse, *Ber.*, 1894, 27, 2409; 1902, 35, 3844) with subsequent purification or isolation of the alcohol products. Alternatively, the hydroxybenzyl alcohols may be part of a crude phenol-formaldehyde--alkali condensation product wherein the alcohol products are not isolated. Or, if desired, the hydroxybenzyl alcohols may be obtained commercially, treated with an aqueous alkaline solution to produce the phenolic salts and then oxidized in accord with the process of this invention.

It is preferred to oxidize hydroxybenzyl alcohols of the formula:

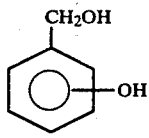

in which the groups are in the ortho-, meta- or para-positions and the benzene nucleus may be further substituted by halogen, alkyl groups of up to 8 carbon atoms, or alkoxy radicals of up to 8 carbon atoms, to the corresponding benzaldehydes.

In a typical pre-treatment run, a fixed bed of a fresh noble metal catalyst on charcoal, contained in a treatment zone, is washed with a batch of basic aqueous feed to remove fine charcoal dust particles. Usually, the basic aqueous feed contains from about 25–30 percent concentration of organics by weight and a 15 percent molar excess of NaOH over organics. Illustratively, the organic material is the reaction product of phenol and formaldehyde in an alkaline medium and the product consists of ortho--hydroxybenzyl alcohol, para-hyroxybenzyl alcohol, 2,4-di(hydroxymethyl)phenol and unreacted phenol. If the unreacted phenol is removed and the organic material consists essentially of ortho- and para--hydroxybenzyl alcohol, the concentration by weight of the organics in the aqueous medium is adjusted to between about 5 percent and 25 percent, to which a 15 percent molar excess of NaOH over organics is added.

After the initial purging of the catalyst bed, the treatment zone is heated to the desired reaction temperature by any conventional means known in the art. One convenient method of heating the treatment zone is the circulation of an appropriate heat exchange medium, such as hot water, within the walls of a jacketed-reaction vessel containing the treatment zone. The treatment zone is then charged with basic aqueous feed which enters at room temperature (about 23° C.) causing the temperature in the treatment zone to fall below the desired level. Because of the temperature drop, the basic aqueous feed is circulated continuously under nitrogen, with heating, until the temperature inside the freshly washed fixed-catalyst bed is within 5° C.–10° C. of the desired reaction temperature, then nitrogen is turned off and air is turned on; this is the zero time of the oxidation reaction. An exotherm reaction occurs when air is initially introduced to the reaction mixture; this exotherm is usually sufficient to bring the reaction temperature to the desired level, approximately 75° C. The desired reaction temperature is maintained by any conventional means (i.e., the same heat exchange apparatus and medium used to heat the treatment zone as previously discussed). The pressure in the reactor is controlled by a regulating valve, and for the purposes of this disclosure is maintained at 120 psig.

The air flow is monitored by a precalibrated differential pressure cell and flows downward through the treatment zone at the rate of 0.07 standard cubic feet per minute (SCFM), unless otherwise indicated. The liquid flow of the aqueous feed is preset on a calibrated pump at approximately 500 cubic centimeters per minute (cc/m) and flows concurrently with air downward through the treatment zone.

When using fresh catalyst there is a difference in the oxidation rates of the ortho- and para-hydroxybenzyl alcohols to the corresponding aldehydes; very little oxidation of the ortho-isomer occurs until approximately one hour after the initial introduction of air or oxygen; whereas after 15 minutes, there is significant oxidation of the para-isomer when the first batch of basic aqueous feed is circulated with air over the fresh catalyst bed. The same starting batch is recirculated over the catalyst bed until at least one of the alcohols in the batch is undetectable by gas chromatography analysis. The alcohols are essentially completely converted to aldehydes, acids or other by-products. Successive and sequential reactions of the catalyst with batches of basic aqueous feed results in the formation of deposits or tar on the catalyst. The noble metal catalyst containing deposits or tar formations as a result of the successive and sequential reactions with the basic aqueous feed is said to be conditioned or activated when the rates or ortho- and para-oxidation are nearly equal. The conditioned catalyst is more selective in the oxidation of the alcohol to the corresponding aldehyde rather than to the corresponding acid; it also increases the rate of formation of the aldehydes and increases the overall product yield. The conditioning process activates the catalyst for an indeterminable period during which the rates of formation and yields of hydroxybenzaldehydes are essentially unchanged. Using conditioned catalyst, the typical yields of ortho-hydroxybenzaldehyde are from 65–85 percent based on the starting amount of ortho-hydroxybenzyl alcohol; the yields of para-hydroxybenzaldehyde are from 90–100 percent based on the starting amount of para-hydroxybenzyl alcohol, as illustrated in Examples 10 to 13 infra.

The following examples illustrate the conditioning of a fresh catalyst by the process of this invention but do not limit the scope of the invention. Parts and percentages are by weight unless otherwise specified.

EXAMPLES 1–5

A series of runs was conducted whereby a catalyst of 0.2 percent palladium-on-charcoal of 4 to 8 Mesh size is used to oxidize aqueous feed resulting from the condensation of phenol with formaldehyde in an alkaline medium. A sufficient amount of 50 percent NaOH is added to the condensation crude to give a 15 percent molar excess of caustic over organics [o-hydroxybenzyl alcohol, p-hydroxybenzyl alcohol, 2,4-di(hydroxymethyl)-phenol (diOH) and unreacted phenol]. The condensation crude treated with NaOH is hereinafter called basic aqueous feed. Prior to the actual oxidation step, 1147 parts of basic aqueous feed is passed through a fixed catalyst bed (1.5 inches in diameter and 24 inches long) to remove fine charcoal dust particles. Then a feed tank is charged with aliquots of the remaining basic aqueous feed which are fed successively to a jacketed reactor containing the fixed catalyst bed under the controlled conditions outlined in Table I below.

TABLE I
Catalyst Conditioning*
0.2 weight % Palladium-on-Charcoal (4–8 Mesh Size)

| Example No. | Quantity of Basic Aqueous Feed (grams) | Circulation Time under Nitrogen Before Start-up | Reaction Time |
|---|---|---|---|
| 1 | 2965 | 30 min. | 3 hrs. |
| 2 | 2398.3 | 15–20 min. | 3 hrs. |
| 3 | 3462.2 | 40 min. | 4½ hrs. |
| 4 | 1158.7 | 15 min. | 2 hrs. |
| 5 | 1162.17 | 15 min. | 2 hrs. |

*The following conditions were held constant for these five examples; Reaction temperature - 75° C.; Air flow - 0.07 SCFM; Liquid Flow - 500 cc/min.; Reaction pressure - 120 psig.

At the termination of each run one or more of the phenolic compounds is undetectable by gas chromatography analysis and the resulting oxidation products are discarded. Gas chromatography analysis of each of the five samples above at approximately 30-minute intervals is reported in Table II below.

TABLE II
Weight % Analysis by Gas Chromatography
(Unreacted phenol, ortho- and para-hydroxybenzoic acid by-products are excluded from this tabulation.)

| Example No. | Reaction Time (minutes) | Hydroxybenzyl Alcohol ortho- | Hydroxybenzyl Alcohol para- | Hydroxybenzaldehyde ortho- | Hydroxybenzaldehyde para- | 2,4-di(hydroxymethyl)phenol |
|---|---|---|---|---|---|---|
|   | 0 | 3.04 | 2.83 | .12 | .47 | 1.63 |
|   | 32 | 2.84 | 1.69 | .06 | 1.28 | 1.07 |
|   | 60 | 2.54 | .69 | .15 | 2.25 | .63 |
| 1 | 91 | 2.01 | .16 | .53 | 2.66 | .31 |
|   | 120 | 1.21 | .07 | .95 | 2.74 | .20 |
|   | 154 | .56 | .02 | 1.39 | 2.72 | .07 |
|   | 181 | .27 | — | 1.55 | 2.79 | .02 |
|   | 0 | 2.46 | 2.71 | .29 | .51 | 1.52 |
|   | 30 | 2.11 | 1.80 | .58 | 1.48 | 1.02 |
|   | 60 | 1.76 | .90 | .84 | 2.30 | .62 |
|   | 95 | 1.17 | .31 | 1.35 | 2.90 | .30 |
|   | 120 | .78 | .15 | 1.50 | 3.01 | .18 |
|   | 150 | .45 | .05 | 1.81 | 3.12 | .06 |
|   | 180 | .28 | .02 | 1.89 | 3.18 | — |
|   | 0 | 2.71 | 2.86 | .36 | .61 | 1.67 |
|   | 30 | 2.54 | 2.18 | .47 | 1.23 | 1.35 |
|   | 60 | 2.24 | 1.42 | .62 | 1.84 | .93 |
|   | 90 | 1.94 | .82 | .82 | 2.42 | .60 |
|   | 120 | 1.49 | .44 | 1.16 | 2.80 | .34 |
| 3 | 150 | .95 | .24 | 1.46 | 2.95 | .15 |
|   | 180 | .50 | .12 | 1.90 | 3.11 | .05 |
|   | 210 | .23 | .04 | 2.18 | 3.20 | — |
|   | 240 | .12 | — | 2.18 | 3.30 | — |
|   | 270 | .06 | — | 2.18 | 3.25 | — |
|   | 0 | 2.46 | 2.62 | .64 | .98 | 1.56 |
|   | 30 | 1.61 | 1.55 | 1.25 | 2.03 | .78 |
| 4 | 60 | .91 | .71 | 1.73 | 2.79 | .29 |
|   | 90 | .34 | .17 | 2.09 | 3.26 | — |
|   | 120 | .10 | .03 | 2.21 | 3.38 | — |
|   | 0 | 2.40 | 2.54 | .66 | .96 | 1.48 |
|   | 30 | 1.73 | 1.76 | 1.19 | 1.77 | .98 |
| 5 | 60 | 1.10 | .96 | 1.60 | 2.52 | .38 |
|   | 90 | .49 | .32 | 1.95 | 3.04 | .08 |
|   | 120 | .16 | .07 | 2.16 | 3.29 | — |

Table II demonstrates the change in oxidation rates of the para- and ortho-hydroxybenzyl alcohols as a function of time using successive batches of basic aqueous feed. Note particularly Example 5 wherein the rate at which the phenolic alcohols being converted to the corresponding aldehydes is nearly equal. The 0.2 percent palladium-on-charcoal catalyst is conditioned and efficiently catalyzes the formation of the desired aldehyde products as demonstrated in the examples which follow.

EXAMPLES 6-12

The same catalyst bed used in Examples 1-5 is flushed with 500 parts of basic aqueous feed to remove materials from previous runs. As in Examples 1-5, the basic aqueous feed results from the condensation of phenol with formaldehyde in an alkaline medium to which is added a 15 percent molar excess of caustic over organics. In a similar manner, after the washing of the catalyst bed, aliquots of the remaining basic aqueous feed are fed successively to the same jacketed reactor containing the same fixed catalyst bed, as in Examples 1-5, under the controlled conditions outlined in Table III below.

Gas chromatography analysis of the oxidation products in Examples 6-9 are recorded at approximately 30-minute intervals and reproduced in Table IV. Table IV also reveals the gas chromatography analysis of the basic aqueous feed at zero reaction time and again at the termination of each run for Examples 10-12; product yields are also reported for Examples 10-12. Table IV succinctly illustrates how the conditioned catalyst is more selective in the oxidation of the alcohol to the corresponding aldehyde rather than the corresponding acid; it also illustrates that the rate of formation of the aldehydes and the overall product yield is increased when compared to Examples 1-5 (oxidation reactions with unconditioned catalyst).

TABLE III

Production of Aldehydes Using Conditioned Catalyst*

| Example No. | Quantity of Basic Aqueous Feed (grams) | Circulation Time under Nitrogen before Start-up | Reaction Time | Reaction Temperature |
|---|---|---|---|---|
| 6 | 1141.2 | 20 min. | 2 hrs. | 85° C. |
| 7 | 1149.03 | 20 min. | 1 hr. 30 min. | 95° C. |
| 8 | 1157.4 | 15 min. | 2 hrs. 45 min. | 65° C. |
| 9 | 1166.07 | 15 min. | 2 hrs. 5 min. | 75° C. |
| 10 | 900.0 | 15 min. | 2 hrs. 15 min. | 75° C. |
| 11 | 1050.0 | 15 min. | 3 hrs. 30 min. | 75° C. |
| 12 | 1000.0 | 15 min. | 3 hrs. | 75° C. |

*0.2 Weight percent Palladium-on-Charcoal (4-8 Mesh Size) used in Examples 1-5 supra. Air Flow - 0.07 SCFM; Liquid Flow - 500 cc/min.; Reactor Pressure - 120 psig; are maintained constantly throughout the above examples.

TABLE IV

Weight % Analysis of Oxidation Product by Gas Chromatography
(Unreacted phenol is excluded from this tabulation.)

| Example No. | Reaction Time (minutes) | Hydroxybenzyl Alcohol ortho- | para- | Hydroxybenzaldehyde ortho- | para- | Hydroxybenzoic Acid ortho- | para- | 2,4(dihydroxymethyl)phenol | Aldehyde Product Yield* |
|---|---|---|---|---|---|---|---|---|---|
| 6 | 0 | 2.71 | 2.89 | .64 | .85 | .10 | — | 1.67 | |
|  | 30 | 1.79 | 1.33 | 1.19 | 2.27 | .17 | .03 | .78 | |
|  | 60 | .65 | .32 | 1.72 | 3.05 | .22 | .06 | .19 | |
|  | 90 | .03 | — | 2.22 | 3.48 | .29 | .04 | — | |
|  | 120 | — | — | 1.82 | 3.33 | .45 | .09 | — | |
| 7 | 0 | 2.45 | 2.40 | .66 | 1.08 | .10 | .03 | 1.48 | |
|  | 30 | 1.51 | .78 | 1.38 | 2.75 | .16 | .02 | .53 | |
|  | 60 | .24 | .06 | 2.04 | 3.36 | .30 | .09 | — | |
|  | 90 | — | — | 2.32 | 3.76 | .52 | .06 | — | |
| 8 | 0 | 2.64 | 2.86 | .42 | .66 | .10 | — | 1.64 | |
|  | 30 | 2.04 | 2.15 | .93 | 1.45 | .17 | .02 | 1.14 | |
|  | 60 | 1.33 | 1.32 | 1.40 | 2.22 | .19 | .02 | .59 | |
|  | 90 | .71 | .65 | 2.11 | 3.15 | .21 | .04 | .22 | |
|  | 120 | .19 | .16 | 2.17 | 3.32 | .23 | .07 | .04 | |
|  | 150 | .02 | .01 | 2.41 | 3.58 | .40 | .07 | — | |
| 9 | 0 | 2.77 | 2.85 | .38 | .72 | .10 | — | 1.70 | |
|  | 30 | 2.00 | 1.74 | .99 | 1.82 | .16 | .03 | 1.14 | |
|  | 61 | .97 | .74 | 1.64 | 2.66 | .12 | — | .41 | |
|  | 90 | .25 | .17 | 2.31 | 3.31 | .21 | .02 | .07 | |
|  | 125 | — | — | 2.28 | 3.38 | .27 | .02 | — | |
| 10 | 0 | 8.87 | 3.3 | — | — | — | — | 6.97 | 66.0% ortho- |
|  | 135 | .16 | .14 | 5.85 | 3.01 | .45 | — | .20 | 91.4% para- |
| 11 | 0 | 6.96 | 4.65 | — | — | — | — | 5.19 | 85.3% ortho- |
|  | 210 | — | — | 5.85 | 4.52 | .61 | — | — | 98.7% para- |
| 12 | 0 | 4.14 | 4.21 | — | — | — | — | 2.54 | 69.4% ortho- |
|  | 180 | — | — | 2.84 | 3.92 | .11 | — | — | 94.1% para- |

*Based on the starting amount of the corresponding alcohol.

EXAMPLE 13

After more than 100 hours of oxidation runs with the same catalyst as in the previous examples, the following oxidation reaction is reported. 1040.11 Parts of basic aqueous feed containing 13.84 percent phenol, 4.57 percent ortho-hydroxybenzyl alcohol, 4.40 percent para-hydroxybenzyl alcohol and 2.88 percent diOH is charged to a feed tank and circulated in a hot-water heated, jacketed-reaction vessel, under nitrogen, until the temperature inside the conditioned, 0.2 percent palladium-on-charcoal catalyst bed is approximately 65° C., then nitrogen is turned off and air is turned on. With the introduction of air, an exotherm reaction causes the temperature inside the reactor to rise to about 75° C. where it is maintained throughout the oxidation process. The air flow is regulated to 0.055 standard cubic feet per minute (SCFM). The pressure in the reactor is maintained at 120 psig. The liquid flow is preset on a calibrated pump at a rate of 500 cubic centimeters per minute. Gas chromatography analysis of the oxidation product at 30-minute intervals is recorded in Table V below:

TABLE V

Weight Percent Analysis of Oxidation Product
>100 Hours of Oxidation Time on Catalyst

| Reaction Time (minutes) | Hydroxybenzyl Alcohol | | Hydroxybenzaldehyde | | Hydroxybenzoic Acid | | DiOH |
|---|---|---|---|---|---|---|---|
| | ortho- | para- | ortho- | para- | ortho- | para- | |
| 0 | 3.49 | 3.51 | .78 | .94 | — | — | 2.17 |
| 30 | 2.67 | 2.67 | 1.52 | 1.78 | — | — | 1.54 |
| 60 | 1.77 | 1.76 | 2.32 | 2.65 | — | — | .88 |
| 90 | .89 | .84 | 3.13 | 3.55 | .13 | .05 | .36 |
| 120 | .23 | .09 | 3.60 | 4.11 | .06 | .09 | .07 |
| 150 | .02 | — | 3.66 | 4.20 | .43 | .21 | — |

This example clearly demonstrates that with the conditioned catalyst, the rates at which the ortho- and para-hydroxybenzyl alcohols are oxidized to the corresponding aldehydes are nearly equal; also the selectivity to the aldehyde rather than acid or other by-products is surprisingly efficient. The product yield is calculated as 81.4 percent ortho- and 97.0 percent para-hydroxybenzaldehyde based on the starting amounts of the corresponding alcohols.

Many variations of the preceding examples may be made without departing from the spirit and scope of the following claims.

What is claimed is:

1. In the process for the selective production of hydroxybenzaldehyde where hydroxybenzyl alcohol in an alkaline aqueous medium is oxidized with molecular oxygen in the presence of a palladium-carbon catalyst to form hydroxybenzaldehyde, the improvement comprising conditioning the catalyst by reacting molecular oxygen with a sufficient quantity of feed comprising a mixture of orthohydroxybenzyl alcohol and parahydroxybenzyl alcohol in an alkaline aqueous medium in the presence of said palladium-carbon catalyst until the rates of oxidation of orthohydroxybenzyl alcohol and para-hydroxybenzyl alcohol are nearly equal whereby the conditioned catalyst is activated and the product yield is increased.

2. The improvement in the process of claim 1 wherein the hydroxybenzyl alcohol is ortho-hydroxybenzyl alcohol.

3. The improvement in the process of claim 1 wherein the hydroxybenzyl alcohol is para-hydroxybenzyl alcohol.

4. The improvement in the process of claim 1 wherein the palladium-carbon catalyst is 0.2 percent palladium-on-charcoal, having a particle size of from 4 to 8 Mesh.

5. The improvement in the process of claim 1 wherein the conditioning of the catalyst comprises the attachment of deposits to the surface of the catalyst, said deposits comprising substantially insoluble reaction products formed by reacting molecular oxygen with a sufficient quantity of feed comprising a mixture of orthohydroxybenzyl alcohol and parahydroxybenzyl alcohol in an alkaline aqueous medium in the presence of said palladium-carbon catalyst until the rates of oxidation of orthohydroxybenzyl alcohol and parahydroxybenzyl alcohol are nearly equal.

6. The improvement in the process of claim 1 or 5 wherein the conditioning of the catalyst is conducted by reacting molecular oxygen with batches of feed and wherein the reaction of each batch of feed is continued until substantially all of one hydroxybenzyl alcohol isomer is oxidized.

* * * * *